US006968221B2

(12) United States Patent
Rosenthal

(10) Patent No.: US 6,968,221 B2
(45) Date of Patent: Nov. 22, 2005

(54) LOW-COST METHOD AND APPARATUS FOR NON-INVASIVELY MEASURING BLOOD GLUCOSE LEVELS

(75) Inventor: Robert D. Rosenthal, Silver Spring, MD (US)

(73) Assignee: Futrex, Inc., Gaithersburg, MD (US)

(*) Notice: Subject to any disclaimer, the term of this patent is extended or adjusted under 35 U.S.C. 154(b) by 243 days.

(21) Appl. No.: 10/387,845

(22) Filed: Mar. 14, 2003

(65) Prior Publication Data

US 2004/0181132 A1 Sep. 16, 2004

(51) Int. Cl.$^7$ .............................................. A61B 5/00
(52) U.S. Cl. ..................................... 600/316; 600/322
(58) Field of Search ............................... 600/310, 322, 600/323, 316

(56) References Cited

U.S. PATENT DOCUMENTS

| 5,077,476 A | | 12/1991 | Rosenthal | |
|---|---|---|---|---|
| 5,086,229 A | | 2/1992 | Rosenthal et al. | |
| 5,435,309 A | * | 7/1995 | Thomas et al. | 600/310 |
| 6,064,898 A | * | 5/2000 | Aldrich | 600/316 |
| 6,505,059 B1 | * | 1/2003 | Kollias et al. | 600/316 |
| 6,549,861 B1 | * | 4/2003 | Mark et al. | 702/76 |

OTHER PUBLICATIONS

Jungheim, Karsten et al., "Glucose Monitoring at the Arm, Diabetes Care, Risky delays of hypoglycemia and hyperglycemia detection," Diabetes Care, vol. 25(6):956-960, Jun. 2002.

Ellison, John M. et al., "Rapid Changes in Postprandial Blood Glucose Produce Concentration Differences at Finger, Forearm, and Thigh Sampling Sites," Diabetes Care, vol. 25(6):961-964, Jun. 2002.

* cited by examiner

Primary Examiner—Eric F. Winakur
(74) Attorney, Agent, or Firm—Rothwell, Figg, Ernst & Manbeck

(57) ABSTRACT

A method and apparatus for measuring a blood analyte concentration using an inexpensive, low precision sensor device is provided. One embodiment of the method includes obtaining energy absorption measurement data through a body part of an individual. A plurality of indicator variables are subsequently calculated from the energy absorption measurement data. An indicator variable from the plurality of indicator variables having the highest correlation to blood glucose level is determined, and a first optical term based on the indicator variable with the highest correlation to blood glucose level is allocated to form a regression analysis equation. An estimated value of the blood analyte concentration using the regression analysis equation is calculated.

30 Claims, 15 Drawing Sheets

| T | F | | T | F | | T | F | | T | F | | T | F | | T | F |
|---|---|---|---|---|---|---|---|---|---|---|---|---|---|---|---|---|---|
| 0 | 0 | | 1.1 | 0.79 | | 2.1 | 0.87 | | 3.1 | 0.62 | | 4.1 | 0.37 | | 5.1 | 0.12 |
| 0.1 | 0.07 | | 1.2 | 0.86 | | 2.2 | 0.85 | | 3.2 | 0.60 | | 4.2 | 0.35 | | 5.2 | 0.10 |
| 0.2 | 0.14 | | 1.3 | 0.93 | | 2.3 | 0.82 | | 3.3 | 0.57 | | 4.3 | 0.32 | | 5.3 | 0.07 |
| 0.3 | 0.21 | | 1.4 | 1.0 | | 2.4 | 0.80 | | 3.4 | 0.55 | | 4.4 | 0.30 | | 5.4 | 0.05 |
| 0.4 | 0.28 | | 1.5 | 1.0 | | 2.5 | 0.77 | | 3.5 | 0.52 | | 4.5 | 0.27 | | 5.5 | 0 |
| 0.5 | 0.36 | | 1.6 | 1.0 | | 2.6 | 0.75 | | 3.6 | 0.50 | | 4.6 | 0.25 | | 5.6 | 0 |
| 0.6 | 0.43 | | 1.7 | 0.97 | | 2.7 | 0.72 | | 3.7 | 0.47 | | 4.7 | 0.22 | | 5.7 | 0 |
| 0.7 | 0.50 | | 1.8 | 0.95 | | 2.8 | 0.70 | | 3.8 | 0.45 | | 4.8 | 0.20 | | 5.8 | 0 |
| 0.8 | 0.57 | | 1.9 | 0.92 | | 2.9 | 0.67 | | 3.9 | 0.42 | | 4.9 | 0.17 | | 5.9 | 0 |
| 0.9 | 0.64 | | 2.0 | 0.90 | | 3.0 | 0.65 | | 4.0 | 0.40 | | 5.0 | 0.15 | | 6.0 | 0 |
| 1.0 | 0.71 | | | | | | | | | | | | | | | |

FIG. 9B

LOW-COST METHOD AND APPARATUS FOR NON-INVASIVELY MEASURING BLOOD GLUCOSE LEVELS

BACKGROUND OF THE INVENTION

1. Field of the Invention

The present invention relates to a low-cost method and instrument for performing non-invasive blood glucose measurements.

2. Description of the Background Art

People with diabetes need knowledge of their blood glucose level in order to determine their medication dosage including the use of insulin. This has led to a large market for invasive and minimally invasive instruments. Such instruments require drawing a small sample of blood, either from the fingertip or other part of the body (e.g., forearm, thigh, etc.). The sample is placed on a chemically treated disposable strip which is inserted into a small battery powered instrument to determine blood glucose level in the body.

There are two disadvantages of the invasive and minimally invasive instruments. First, there is the pain and discomfort of making a measurement, particularly at a fingertip site, and second, the disposable test strips are costly (e.g., 70¢ per strip).

Although the minimally invasive instruments may eliminate a majority of the discomfort associated with making a measurement, the glucose level of interstitial fluid that is drawn at sites away from the fingertips may be significantly different from the true blood glucose level as there is a significant time delay before the glucose level of the interstitial fluid adjusts to the actual blood glucose level. This causes potentially serious, and even medically-threatening, measurement errors. In particular, such errors can be significant when the glucose is rapidly falling into the hypoglycemic range, as disclosed in "Glucose Monitoring at the Arm: Risky Delay of Hypoglycemic and Hyperglycemia Detection," Jungheim, K. et al., Diabetes Care, Vol. 25, No. 6, pp. 956–60 (June 2002), which is incorporated herein by reference.

Further, interstitial fluid instruments can be in error by as much as 100 to 150 mg/dL compared to true blood glucose in the first ninety minutes following the consumption of a meal, as disclosed in "Rapid Changes in Postprandial Blood Glucose Concentration Differences at Finger, Forearm, and Thigh Sampling Sites," Ellison, J. M. et al., Diabetes Care, Vol. 25, No. 6, pp. 961–64 (June 2002), which is incorporated herein by reference. Even if the above errors were tolerable, the test strips for the minimally invasive instruments cost approximately the same as the test strips for the invasive (fingertip) instruments.

Non-invasive instruments for measuring blood glucose levels are desirable and are well known in the art. For example, U.S. Pat. No. 5,077,476 issued on Dec. 31, 1991 to Rosenthal and U.S. Pat. No. 5,086,229 issued on Feb. 4, 1992 to Rosenthal, both incorporated herein by reference in their entirety, use near-infrared quantitative technology for making such measurements. Both patents disclose using a near-infrared energy source (e.g., IRED) for introducing near-infrared energy into a test subject's finger.

One limiting aspect of the near-infrared quantitative non-invasive measurement of blood glucose is that it requires a very precise optical measurement at multiple wavelengths (e.g., eight or more wavelengths). The required precision and the large number of required measurement wavelengths makes such an instrument complex and potentially costly.

Another limiting aspect is that the calibration system performs a multiple regression analysis to calculate the calibration constants. Although the multiple linear regression analysis has great value, it requires a large number of calibration samples, and it limits subsequent glucose measurements to the range of calibration samples.

Thus, there is a need for a low cost non-invasive method and apparatus, which requires a small number of calibration samples, for measuring the blood glucose concentration in blood.

SUMMARY OF THE INVENTION

The invention provides an inexpensive method for measuring a blood analyte concentration. Energy absorption measurement data is obtained through a body part of an individual. A plurality of indicator variables are calculated from the energy absorption measurement data. An indicator variable from the plurality of indicator variables having the highest correlation to blood glucose level is determined, and a first optical term based on the indicator variable with the highest correlation to blood glucose level is allocated to form a regression analysis equation. An estimated value of the blood analyte concentration using the regression analysis equation is calculated.

According to another aspect of the invention, an inexpensive non-invasive measurement instrument for measuring a blood analyte concentration is provided. A first light source introduces near-infrared energy into blood present in a body part of an individual, and a second light source introduces red light energy into the blood present in the body part. A detector detects the energy emerging from the body part, and produces an electrical signal indicative of the energy emerging from the body part. A processor calculates a plurality of indicator variables from the electrical signal, determines which indicator variable from the plurality of indicator variables has the highest correlation to blood glucose level, and calculates an estimated value of the blood analyte concentration based on the indicator variable having the highest correlation to blood glucose level. The blood analyte concentration is calculated using a regression analysis equation.

According to yet another aspect of the invention, an inexpensive method for measuring a blood analyte concentration is provided. Energy absorption measurement data is obtained through a body part of an individual, and an indicator variable is calculated from the energy absorption measurement data. A first optical term is allocated based on the indicator variable to form a regression analysis equation, and an estimated value of the blood analyte concentration is calculated using the regression analysis equation. The indicator variable is at least one of a pulse rate, LED pulse strength, IRED pulse strength, LED normalized pulse strength, IRED normalized pulse strength, pulse strength ratio, normalized pulse strength ratio, Delta OD, Delta OD divided by average LED Log 1/T, Delta OD divided by average IRED Log 1/T, Delta OD divided by average LED Log 1/T and average IRED Log 1/T, meal data, and occluded measurement data.

According to still another aspect of the invention, an inexpensive non-invasive measurement instrument for measuring a blood analyte concentration is provided. A first light source introduces near-infrared (NIR) energy into blood present in a body part of an individual. A second light source introduces red light energy into the blood present in the body part. A first detector detects the NIR energy emerging from the body part, and produces a first electrical signal indicative of the NIR energy emerging from the body part. A second detector detects the red light energy emerging from the body part, and produces a second electrical signal indicative of the red light energy emerging from the body part. A processor calculates a plurality of indicator variables from the first electrical signal and the second electrical signal, determines which indicator variable from the plurality of indicator variables has the highest correlation to blood glucose level, and calculates an estimated value of the blood analyte concentration based on the indicator variable having the highest correlation to blood glucose level. The blood analyte concentration is calculated using a regression analysis equation.

The above and other features and advantages of the present invention will be further understood from the following description of the preferred embodiments thereof, taken in conjunction with the accompanying drawings wherein like reference numerals are used throughout the various views to designate like parts.

BRIEF DESCRIPTION OF THE DRAWINGS

FIG. 9B is a table representing the curve graphically illustrated in FIG. 9A.

DETAILED DESCRIPTION OF THE PREFERRED EMBODIMENTS

In accordance to the present invention, only a single infrared emitting diode (IRED) and a single light emitting diode (LED) (i.e., two wavelengths) are required for non-invasively measuring blood glucose levels. In general, conventional non-invasive instruments for measuring blood glucose levels require multiple IREDs (typically 10–14), each IRED with an expensive narrow band pass optical filter to generate multiple wavelengths for determining blood glucose levels. Such prior non-invasive instruments are large and expensive.

In an embodiment of the method utilizing a measurement instrument having a single IRED and a single LED, it allows without the need of any expensive optical narrow band pass filters, near-infrared (near-IR) energy and red light energy to be introduced into blood present in a body part of a test subject. The energy emerges from the test subject generally opposite from the IRED and LED. After determining an measurement parameter (or indicator variable) with a meaningful or highest correlation to blood glucose level from several indicator variables, an estimated value of blood analyte concentration is calculated using an regression analysis equation. By eliminating the prior art need for a large number of LEDs/IREDs, each with its own narrow band pass optical filter, avoids the large energy loss encountered by forcing all LED/IRED light to intersect the body part at the same point. Accordingly, a smaller and lower cost optical silicon detector can be realized.

Figure 1:
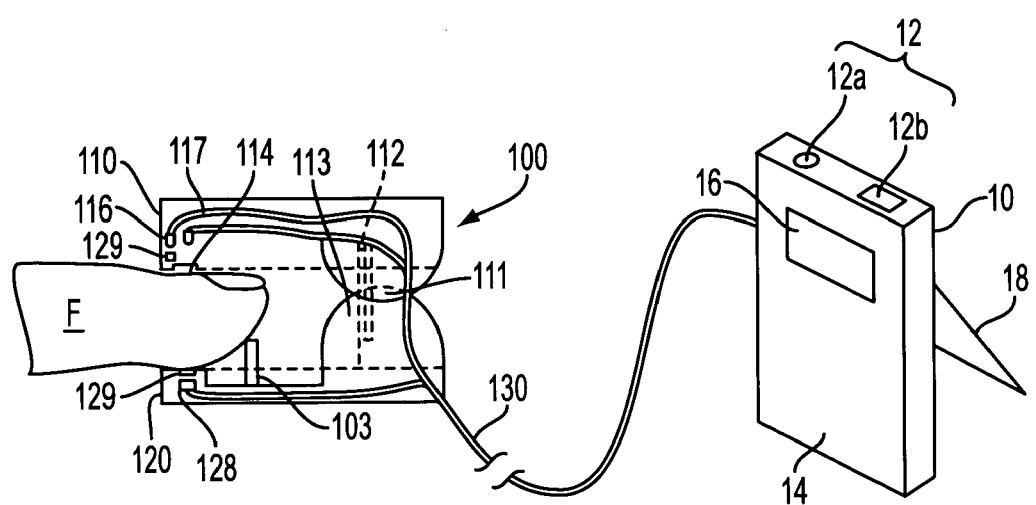
FIG. 1 shows an exemplary embodiment of a measurement device for performing non-invasive blood glucose measurements according to the present invention.

In the non-invasive measurement instrument for estimating blood glucose according to the present invention illustrated in FIG. 1, included is a probe 100 adapted to be placed over a finger F of a test subject. The probe 100 has an IRED 116 (e.g., 905 nm) and a LED 117 (e.g., 662 nm) disposed within an upper flange 110. The inwardly-facing surface of the upper flange 110 is provided with an optically clear window 114 for placement against the subject's finger F.

The upper flange 110 is hinged about a shaft 111 to a lower flange 120, and a spring 112 serves to maintain the flanges 110, 120 in a closed position. An optical detector 128 is disposed in the lower flange 120 opposite the IRED 116 and LED 117. The detector 128 is disposed behind an optional window 129. A finger stop 103 positions and maintains the subject's finger F in a proper position within the probe 100. Each of the flanges 110, 120 is provided with light-shielding barriers 113 (shown in phantom) to block ambient light from entering the probe 100.

The probe 100 is electrically connected to a separate chassis unit 10. The electrical signals produced by the detector 128 are transmitted via line 130 to the chassis unit 10. The chassis unit 10 includes a power source (not shown), an input device 12, a processor unit 14, and a display unit 16. Since the processor unit 14 and display unit 16 are in a separate device from the silicon detector 128, the non-invasive measurement instrument is user friendly.

The processor unit 14 includes a microprocessor, data storage, display driver and other circuitry. The input device 12 may include an input button (digital potentiometer) 12a for entering meal data (e.g., relative meal factor and meal intensity) displayed on the display unit 16, and an data entry button 12b for entering data into the microprocessor. The input button 12a may also be used to set the current time and date.

The display driver provides a signal to the digital display unit 16 for notifying and directly displaying the estimated amount of glucose present in the test subject's blood. It will be appreciated that an individual may be notified of the estimated amount by an audio means, in addition or alternatively to the visual notification.

The chassis unit 10 can be supported by a stand 18. Further, a warning device (not shown) can be configured into the chassis 10 for notifying a user of dangerous blood glucose levels. The warning device may include a buzzer sound, a warning lamp, a warning message (audio or visual), or the like. In addition, the warning device may be located at a position where the individual can easily receive the warning.

Figure 12:
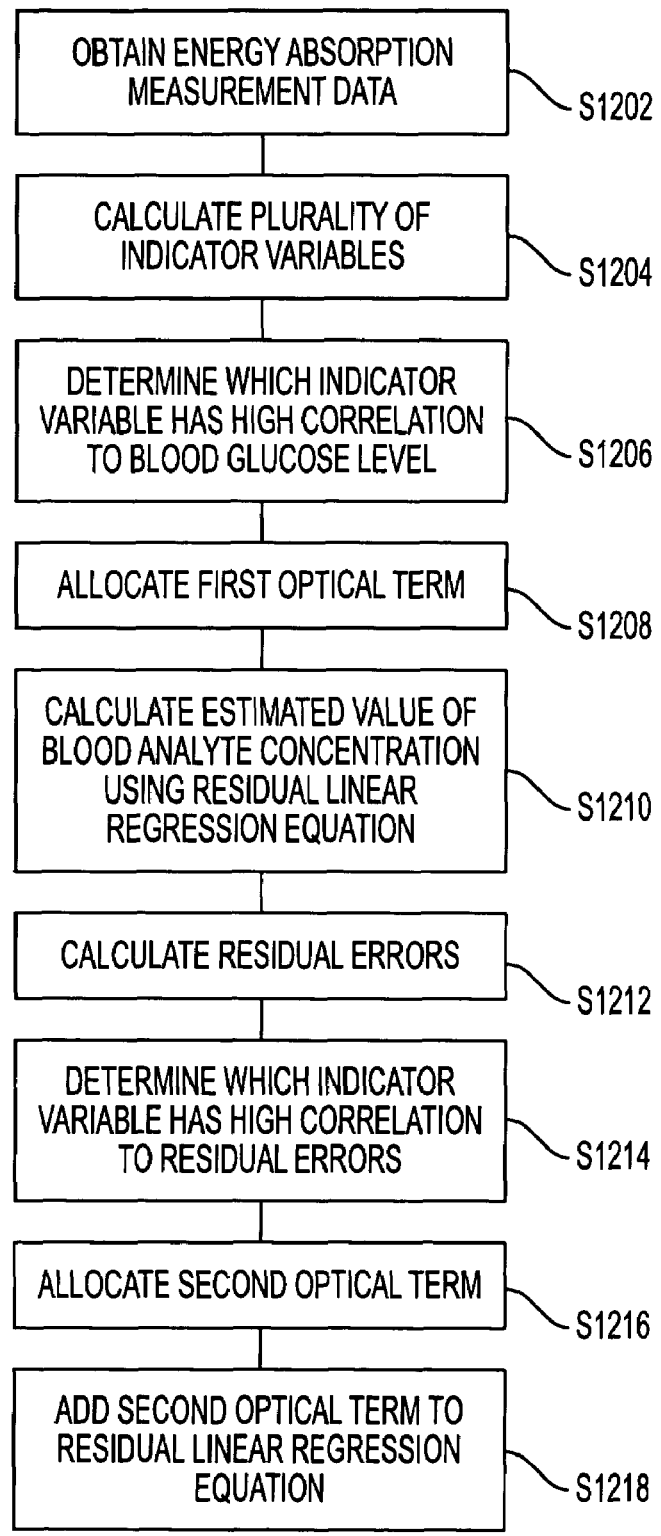
FIG. 12 is a flow chart of a method of non-invasively measuring blood glucose levels according to the present invention.

In operation, as illustrated in FIG. 12, the finger F of the test subject is inserted between the flanges 110, 120 of the probe 100. The test subject must be electrically grounded before measurements are taken. Light energy emitted by the IRED 116 and LED 117 is transmitted through the finger F, and then detected by the optical detector 128 (step S1202). In the preferred embodiment, only two wavelengths are used to perform the non-invasive measurement (e.g., one wavelength in the red portion of the spectrum and one wavelength in the near-infrared (near-IR) portion of the spectrum). Using the information detected by the detector 128, an measurement parameter or several measurement parameters (e.g., pulse rate, pulse strength, etc.) are calculated (step S1204). Electrical signals, which are representative of the energy emerging from the body part, the pulse rate, the pulse strength, etc., are then transmitted via line 130 to the chassis unit 10, and may be stored in the data storage.

The processor unit 14 selects the measurement parameter with the highest correlation to blood glucose level to form a regression analysis equation (steps S1206 and S1208). In the preferred embodiment, the regression analysis equation is a linear residual regression equation. However, it will be appreciated by those skilled in the art that a linear regression equation, multiple linear regression equation, or the like, can be used. The processor unit 14 uses the regression analysis equation stored in the data storage to yield an estimated or predicted value of the blood analyte concentration (step S1210). The blood glucose level is displayed on the display unit 16, for example, in a digital format.

In the preferred embodiment, the IRED 116 and LED 117 are alternately cycled on and off so that each is turned on a few milliseconds before its measurement is made and then turned off. These alternating cycles continue for at least 4 to 15 seconds to allow at least four pulse cycles to occur. At that time, the IRED 116 and LED 117 are turned off, thereby significantly decreasing the measurement instrument's power demand which increases the power source's life. However, the IRED 116 and LED 117 can be consecutively cycled on and off. It will be appreciated by those skilled in the art that the measurement instrument can also be used by simply turning on the IRED 116 and LED 117 steady state and making periodic A/D conversions (e.g., ten per second). This approach, however, requires two independent detectors, each with an appropriate narrow band pass optical filter, one of which tuned to the IRED 116 and the other tuned to the LED 117. Using only one IRED and one LED allows optically measuring the finger pulse signal many times during a pulse cycle.

Figure 2:
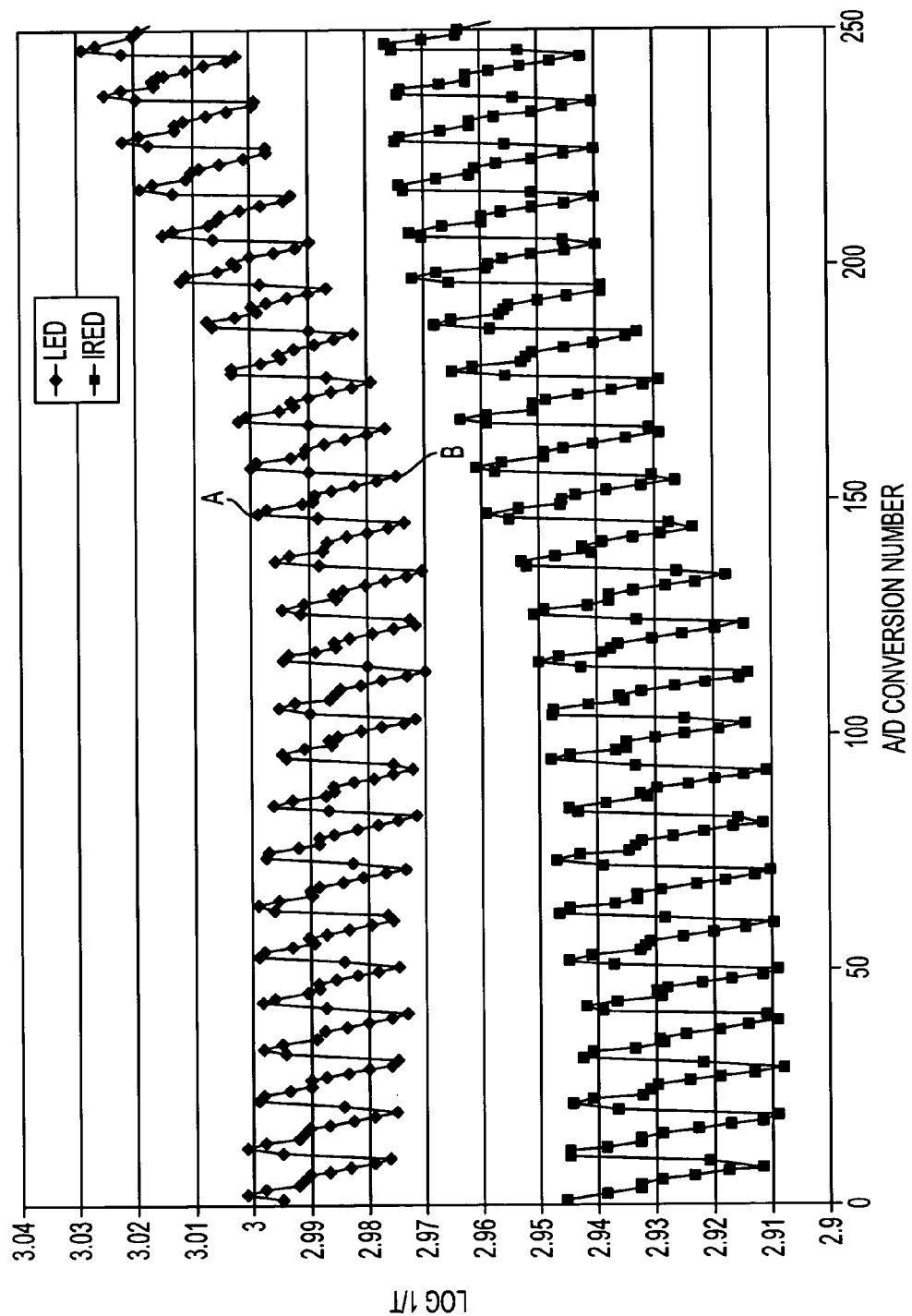
FIG. 2 shows pulse measurements of a test subject taken during a pulse cycle when light energy is alternately emitted by both an IRED and a LED.

FIG. 2 shows the pulse when light energy is alternately emitted by the IRED 116 and LED 117. There are approximately 12 to 30 optical measurement points in a single pulse cycle. In the graph, the vertical axis is a logarithmic measure of light energy reaching the detector 128 (Log 1/T, wherein T is the fraction of the light that passes through the finger F and reaches the detector 128). The horizontal axis is a linear measure of time shown in terms of the number of analog to digital converter counts ("A/D counts"). The linear measure is 250 A/D counts, which is approximately 16 seconds.

When infrared light generated by the IRED 116 and red light generated by the LED 117 are transmitted through a subject's body part, the optical detector 128 measures how much optical energy is absorbed by the finger F. Each time the heart beats, additional blood is surged through the body, including the blood capillaries in the fingertip. This periodic surge of blood, normally called pulse beat or heart rate, causes the finger F to become more optically opaque, thereby producing the cyclic pattern in FIG. 2 for both the IRED 116 and LED 117. The detector 128 produces an electrical signal of the pulse measurements, and the signal is transmitted via line 130 to the chassis unit 10. The signal may be stored in the data storage.

Figure 3:
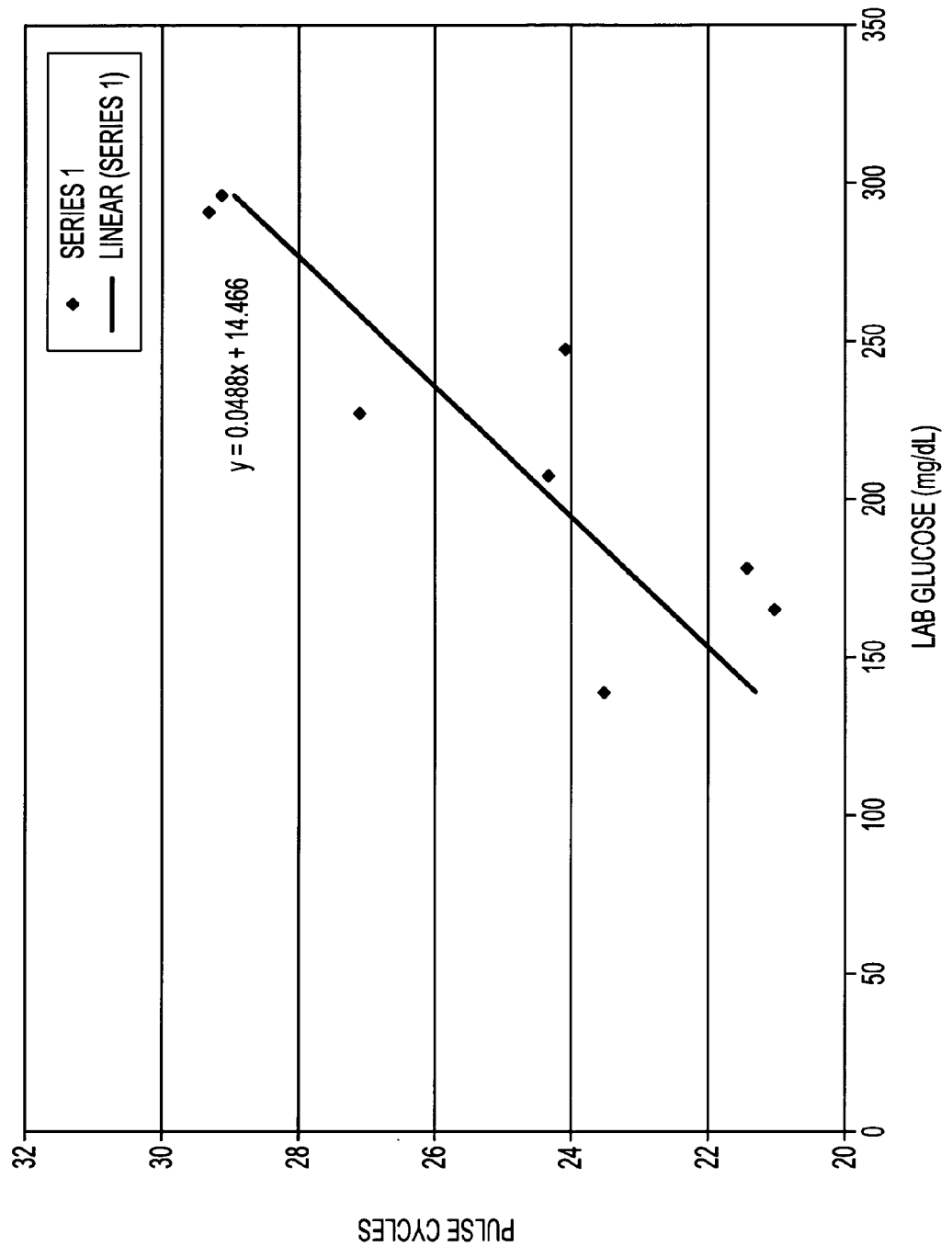
FIG. 3 is a graph illustrating pulse rate calculation using the detected pulse measurements of the test subject illustrated in FIG. 2.

A pulse beat measurement can be calculated using the pulse measurements detected by the detector 128 (e.g., using light energy emitted by the IRED 116 and LED 117) in order to determine an optical term with a meaningful correlation to blood glucose level. In other words, the pulse rate measurement may be easily measured by the non-invasive measurement device (e.g., a fingertip pulse monitor). FIG. 3 illustrates a pulse rate calculation using the detected pulse measurements of FIG. 2. The vertical axis in FIG. 3 represents the number of pulse cycles, and the horizontal axis represents a measure of laboratory determined blood glucose. The scatter diagram illustrates a correlation of 0.844 between the number of pulse cycles in the 16 second time period with laboratory determined blood glucose level. As shown, this pulse rate measurement provides a meaningful correlation to blood glucose level. The detector 128 produces an electrical signal indicative of the pulse rate and transmits the signal to the chassis unit 10, which may be stored in the data storage.

Figure 4:
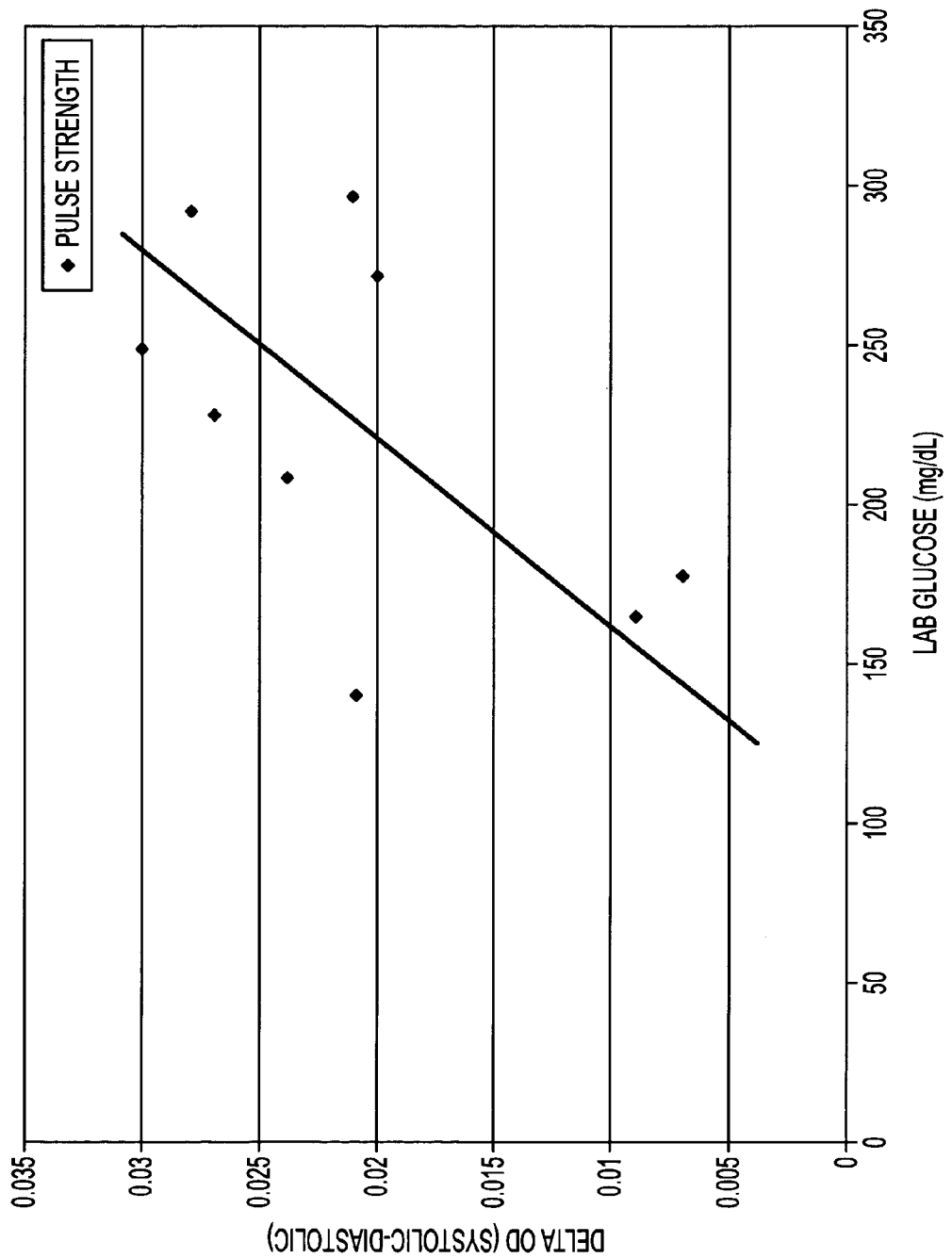
FIG. 4 is a graph illustrating the correlation of pulse strength to laboratory determined blood glucose when light energy is emitted by the LED.
Figure 5:
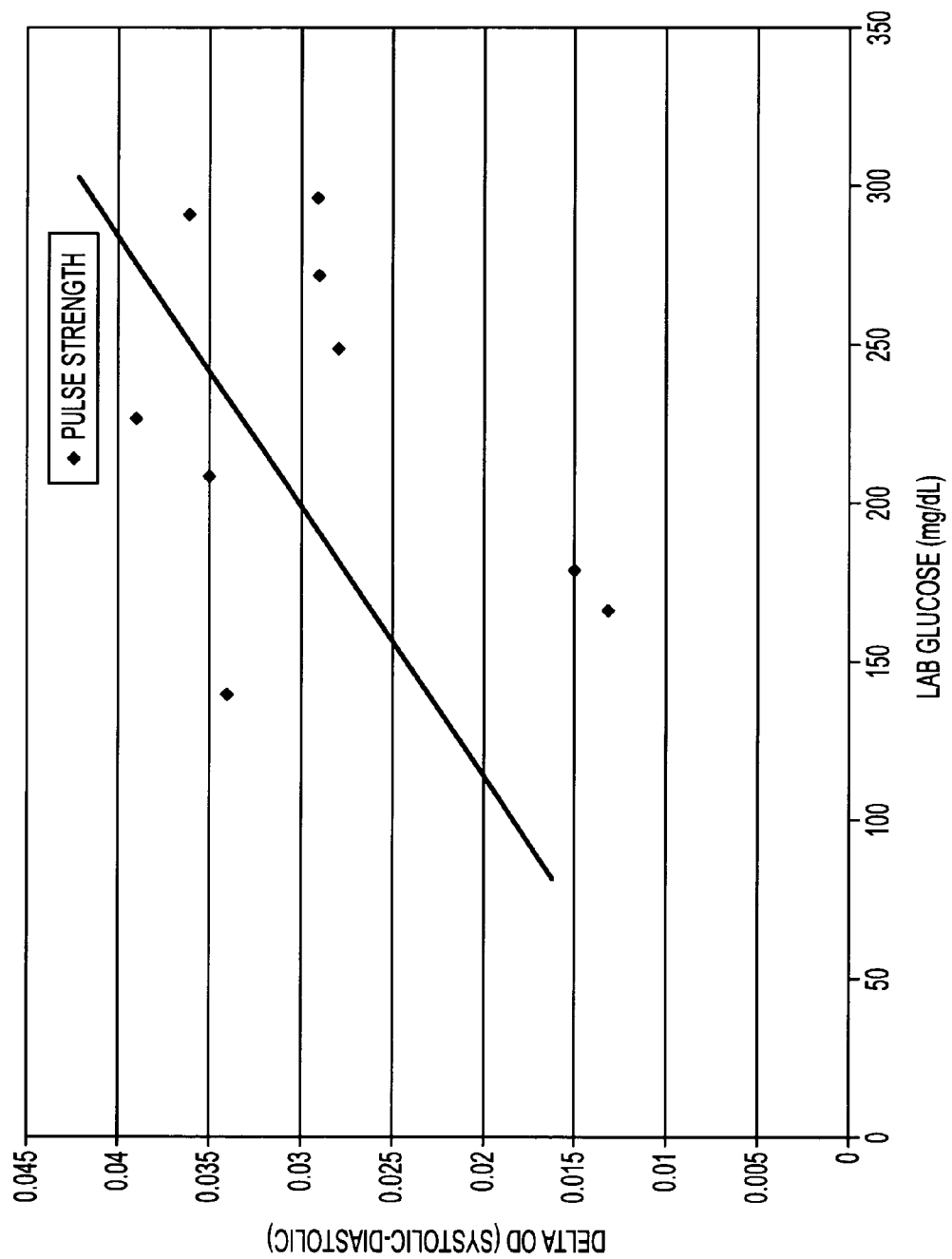
FIG. 5 is a graph illustrating the correlation of pulse strength to laboratory determined blood glucose when light energy is emitted by the IRED.

A pulse strength measurement can also be calculated using light energy emitted by the IRED 116 and LED 117 in order to determine an optical term with a meaningful correlation to blood glucose level. The pulse strength measurement is defined as the average systolic level "A" (FIG. 2) minus the average diastolic level "B" (FIG. 2). FIGS. 4 and 5 illustrate the relationship between the LED's pulse strength and laboratory blood glucose level, and the IRED's pulse strength and laboratory blood glucose level, respectively. The vertical axis is a measure of Delta OD (Systolic-Diastolic), and the horizontal axis is a measure of laboratory determined blood glucose.

Referring to FIG. 4, the correlation between the LED 117 average pulse strength and the laboratory blood glucose level (as measured from FIG. 3) was 0.537. Referring to FIG. 5, the correlation between the IRED 116 average pulse strength and the laboratory blood glucose level (as measured from FIG. 3) was 0.372. The correlation of pulse strength to laboratory blood glucose level is approximately 0.25 or higher on most individuals. Although this correlation is small, it is statistically significant. Similarly, this information is calculated in the chassis unit 10, which may be stored in the data storage.

Figure 6:
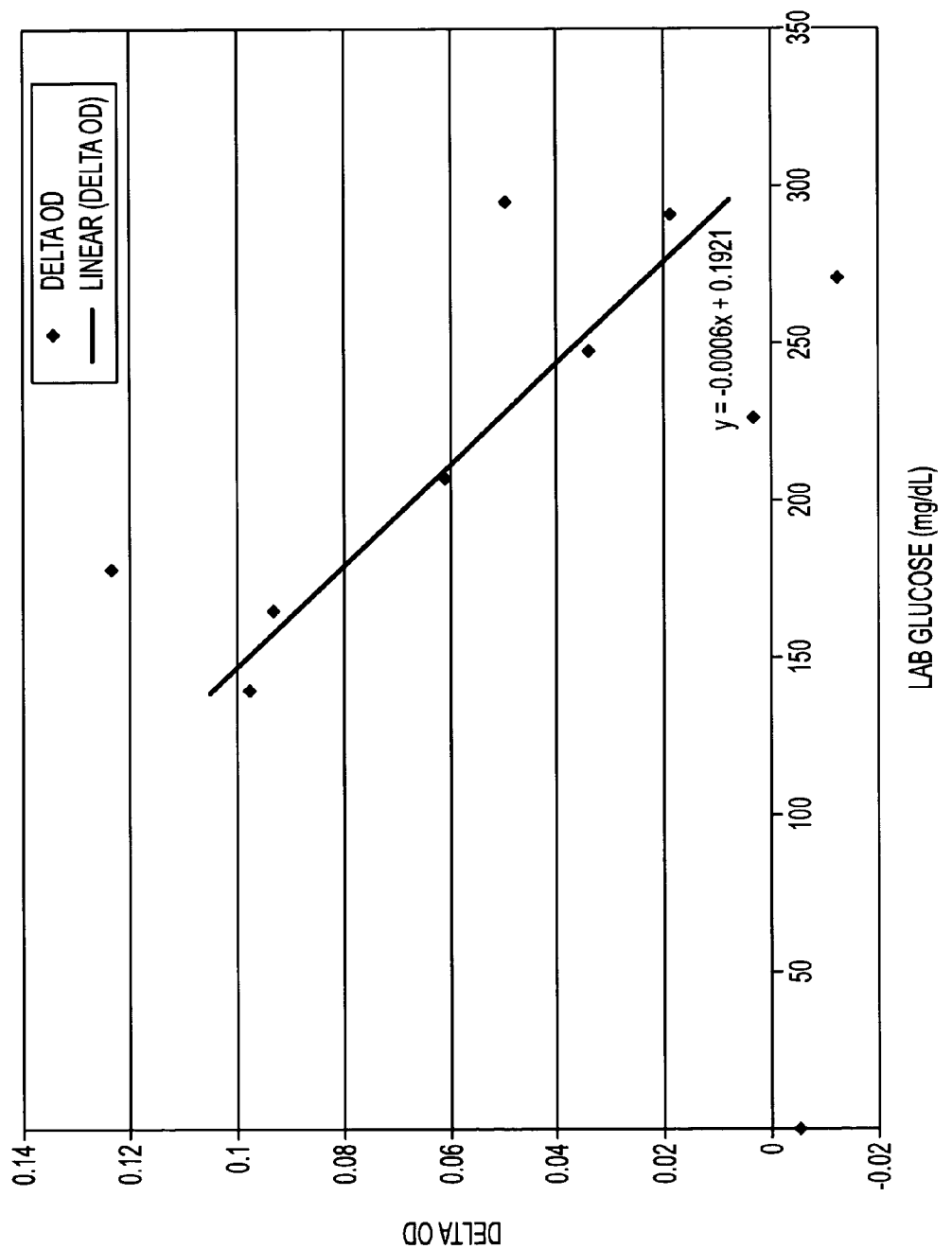
FIG. 6 is a graph illustrating another example of an optical relationship between the IRED and LED, and laboratory determined blood glucose.

FIG. 6 illustrates another example of an optical relationship between the light sources 116, 117 and laboratory determined blood glucose, which can be used to determine an optical term with a meaningful correlation to blood glucose level. The vertical axis is a measure of Delta Log 1/T which is the average of all the IRED readings of FIG. 3 subtracted from the average of all the LED readings of FIG. 3. The horizontal axis is a measure of laboratory determined blood glucose. In FIG. 6, the relationship between the difference of the Log 1/T values of the IRED 116 and LED 117 has a correlation to blood glucose of approximately 0.739. The offset of the line is 0.1921 and the slope of the line is −0.0006. This information is calculated in the chassis unit 10, and may be stored in the data storage.

As discussed above, a test subject's pulse rate, pulse rate, or the like, can be used to calculate an estimated value of blood analyte concentration. Prior to calculating the estimated value of blood analyte concentration, however, a calibration procedure is performed. The calibration procedure requires an individual to perform comparative measurements at a test site; preferably, the fingertip on the opposite hand from the blood draw.

In the preferred embodiment, a residual calibration approach is used as the calibration procedure. It will be appreciated by those skilled in the art that a multiple linear regression approach, partial least square approach, or the like, may be used. The residual calibration approach allows an individual to perform approximately ten comparison measurements between one of the previously and subsequently described optical parameters (e.g., pulse rate, pulse strength, etc.) and the laboratory blood glucose. The ten comparison measurements can be performed in a single day or over a period of several days.

The residual calibration approach, as defined in equation (1), is based upon a simple linear regression equation using the optical term that provides a meaningful (or the highest) linear regression coefficient with laboratory glucose.

$$\text{Predicted Glucose} = K0 + K1(S) \qquad \text{Equation (1)}$$

S is the optical term that has the highest correlation with laboratory glucose. K0 and K1 are the offset and the slope (i.e., the calibration constants determined by the linear regression analysis). The residual calibration approach allows comparing of the predicted blood glucose level of each calibration sample to the laboratory glucose values.

Figure 7:
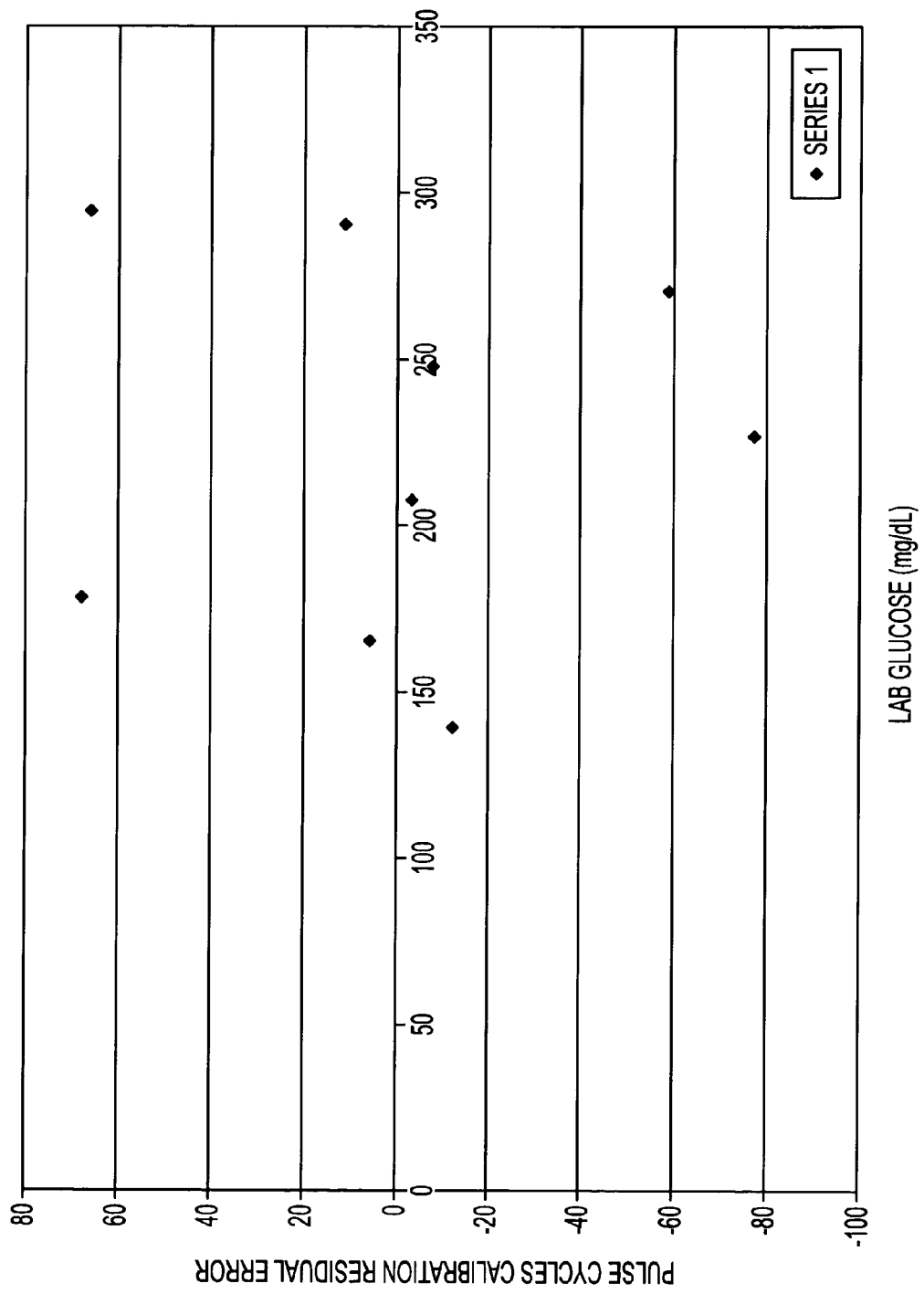
FIG. 7 shows the residual errors of the calibration procedure using the data from FIG. 3.

By way of example, using the optical terms calculated in FIGS. 3–6, the pulse rate determined from FIG. 3 provided the highest linear regression correlation with blood glucose level. K0 and K1 are the offset and slope, respectively, of the line in FIG. 3. In this case, K0 is 14.466 and K1 is 0.0488. Residual errors are determined using the measurement parameter with the highest correlation to blood glucose level (step S1212). FIG. 7 shows the residual errors of the calibration procedure using the pulse rate data from FIG. 3.

A second simple linear regression is performed individually for each of the unused optical terms (e.g., pulse rate, pulse strength, etc.) (steps S1214 and S1216). The purpose of these linear regression coefficients are to identify which optical term best diminishes the residual errors, for example, to determine which unused optical term provides the highest correlation coefficient (e.g., the lowest standard error) for the residual error terms. The residual regression term "C0+K2 (R)" is added to Equation (1) as shown below (step S1218).

$$\text{Predicted Glucose} = K0 + K1\ (S) + C0 + K2\ (R) \qquad \text{Equation (2)}$$

The term R is the optical term that provides the highest correlation to the residual errors of Equation (1). C0 is the offset of the residual linear regression equation. K2 is the slope of the residual linear regression equation. The two offset terms can be combined.

Equation (2) is then used to predict the glucose level of the calibration samples and a new set of residual errors are determined. These new residual errors will be less than the previous errors since the term R has been added to Equation (2). It will be appreciated by those skilled in the art that additional terms using different optical parameters can be added to Equation (1) to still further reduce the residual error.

Figure 8:
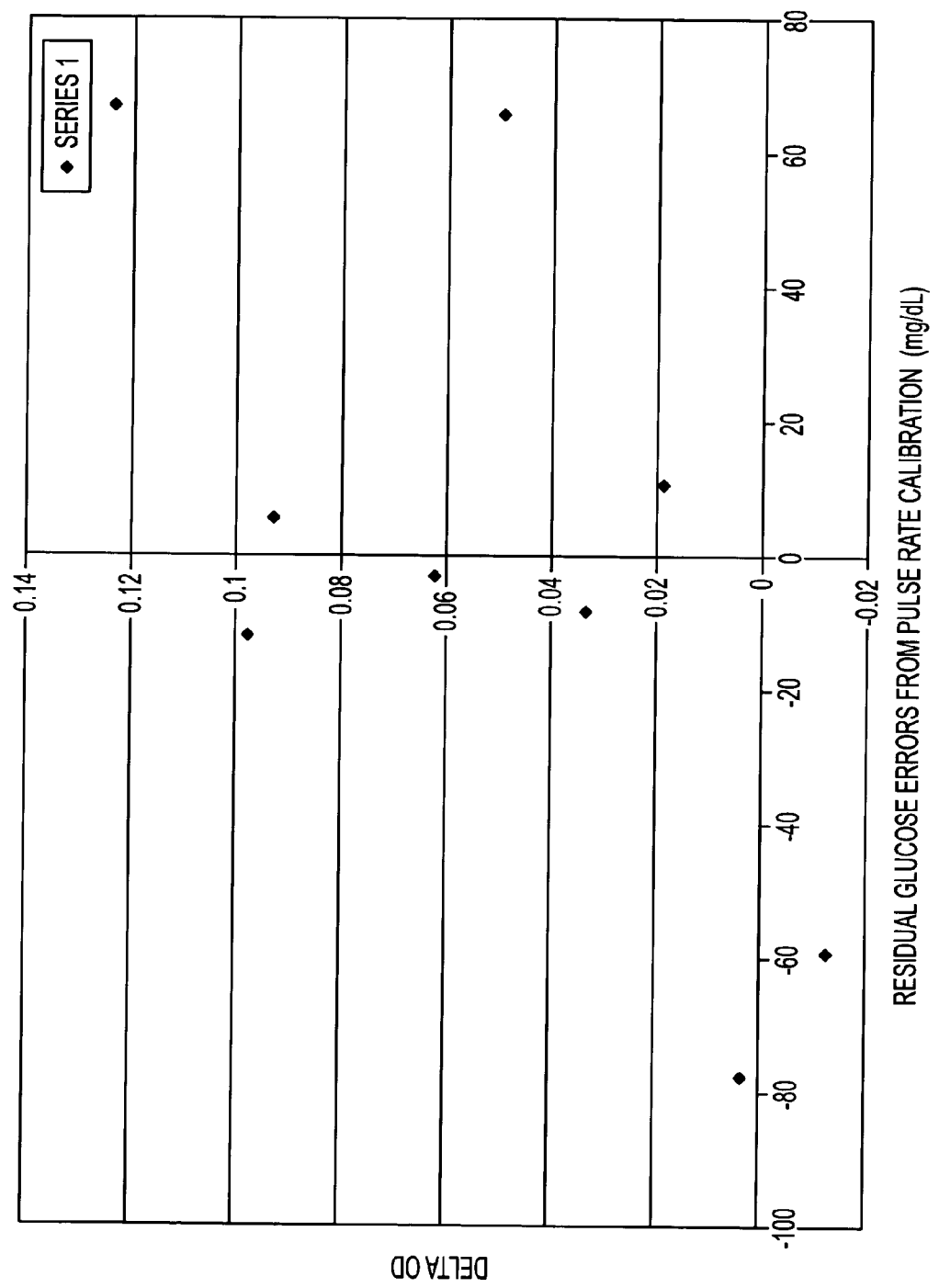
FIG. 8 shows the outcome of using a single residual term in a residual linear regression equation.

FIG. 8 graphically illustrates the outcome of using one residual term in Equation (1). As illustrated in FIG. 8, blood glucose is predicted based on samples measured after the calibration procedure is completed. In order to reliably use the calibration approach of the present invention, the following must be satisfied:

the range of laboratory glucose values during the calibration (e.g., the highest minus the lowest glucose sample) must be equal to or greater than 140 mg/dL, a minimum of 25% of the calibration samples must be below, and a minimum of 25% of the calibration samples must be above, the average glucose of all the samples, a minimum of 10 samples must be used in the calibration, and the primary optical term used in Equation (1) must have a correlation of 0.7 or higher.

The estimated or predicted blood glucose method and measuring instrument according to the present invention is inexpensive and sufficient in determining the dosage of insulin or other medication in the typical home environment.

In another embodiment, meal data is another optical term that can be analyzed by the linear regression equation to predict blood glucose measurement. The time after the consumption of a meal combined with the intensity of the meal has a significant correlation to blood glucose level.

Figure 9A:
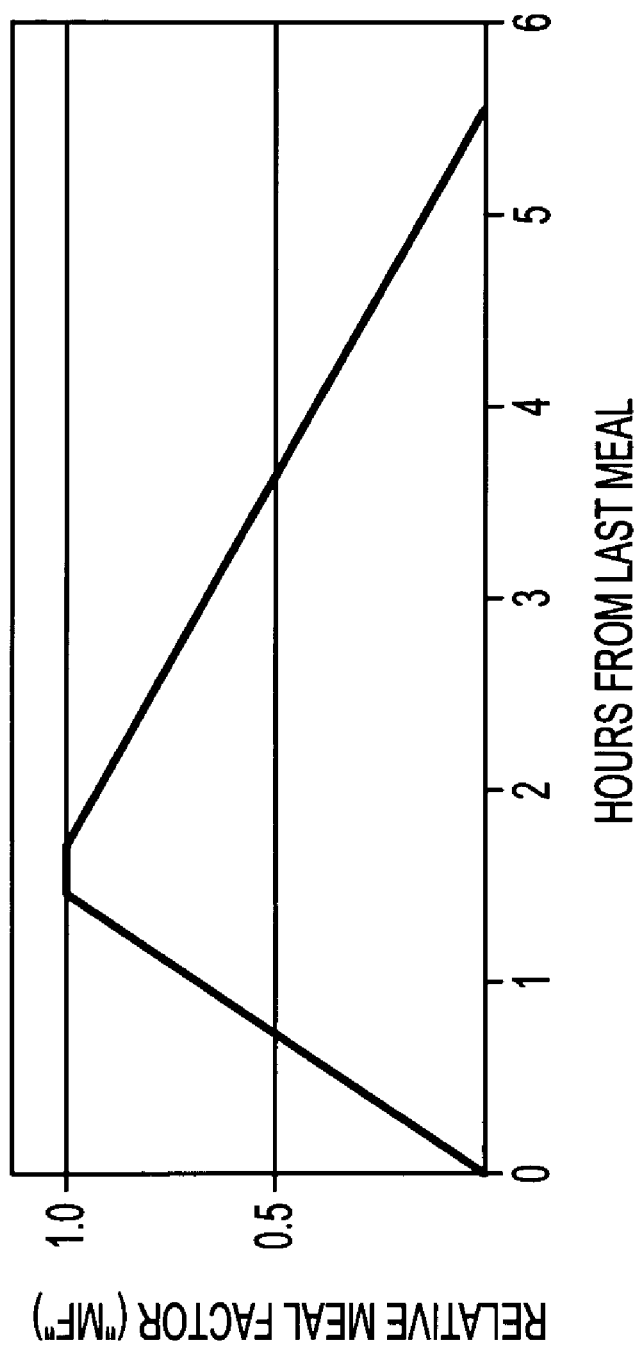
FIG. 9A is an idealized response curve of the impact on blood glucose level after the consumption of a meal over a period of time.

FIG. 9A is an idealized response curve of the impact on blood glucose level after the consumption of a meal. FIG. 9B is a table in tubular form of the curve graphically illustrated in FIG. 9A. The curve and table represent a typical blood glucose response, and is not the response of any particular person. The curve shows that blood glucose level increases at a substantially steady or linear rate following the consumption of a meal, and peaks between approximately one and two hours after the meal. A meal is defined as an intake of nutrients that causes a rise in a blood analyte, such as glucose, of at least 50 mg/dL in two hours. The blood glucose level thereafter decreases at a substantially steady rate. The decreasing portion of the curve represents the absorption of blood glucose into the cells of the body, and shows the decrease of blood glucose levels as the blood glucose is consumed by the body. The curve shows that the rate of decrease of blood glucose level is about one third the rate of increase of blood glucose level.

Meal data f is defined by Equation (3), wherein:

$$f = \text{Log}(MF*I) \qquad \text{Equation (3)}$$

MF is the relative meal factor. I is the intensity of the meal on a scale of 1 to 10; 8 being be the value for the typical largest meal of the day based upon its carbohydrate content. It will be appreciated by those skilled in the art that the relative meal factor and intensity of the meal can be defined in several ways to determine the meal data f. High carbohydrate meals increase blood glucose to higher levels as compared to meals of much lesser ingested energy.

Figure 9C:
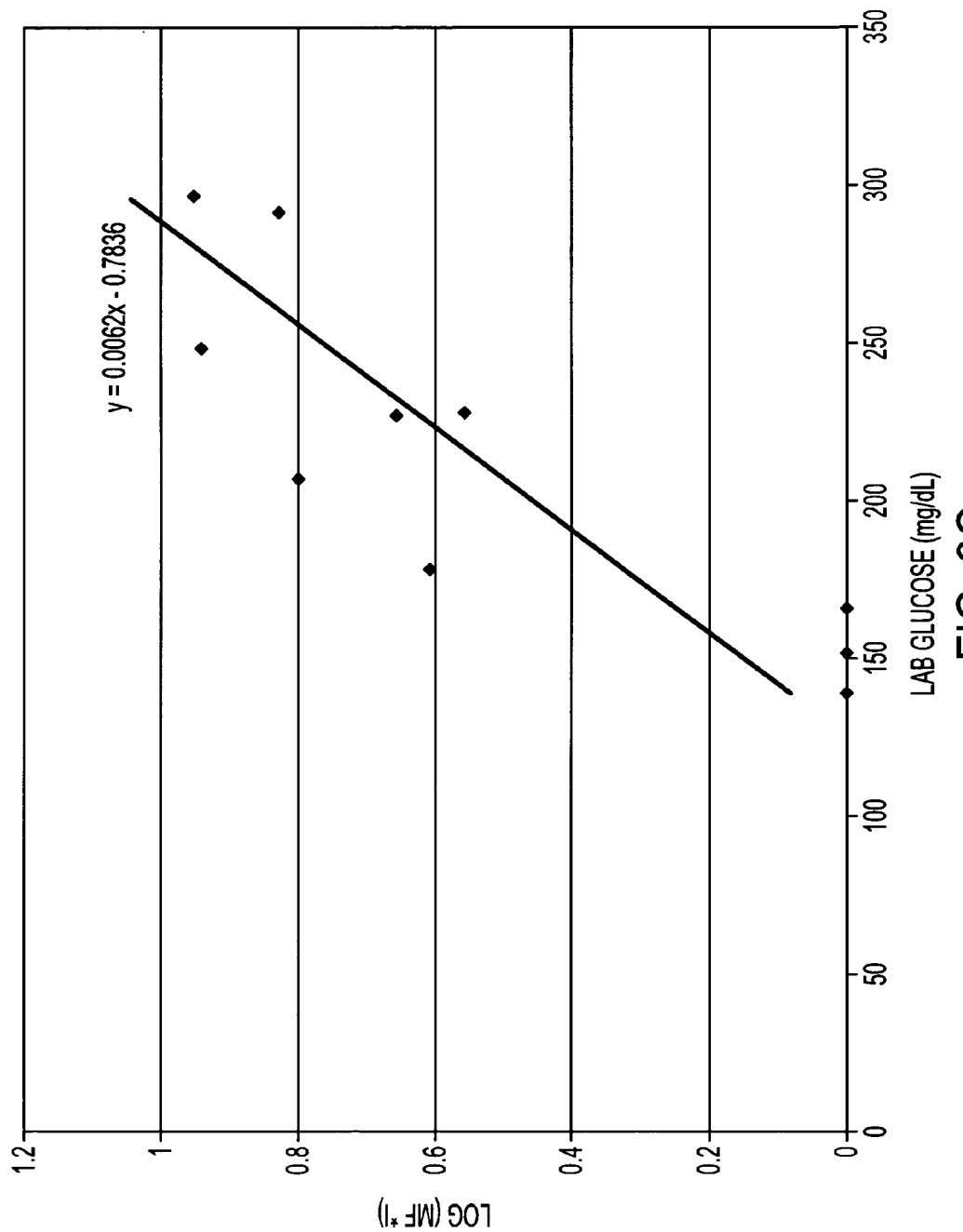
FIG. 9C is a graph of Log (MF*I) as a function of laboratory determined blood glucose.

In Equation (3), the meal factor MF is multiplied by the intensity of the meal I. Taking the logarithm of the resultant (MF*I) provides a meaningful correlation to the glucose presence in the blood stream. If a substantial amount of time has passed since eating a meal (e.g., eight hours), then the resultant (MF*I) would be equal to zero, which is an invalid number to derive a logarithm. If this occurs, the logarithmic answer is arbitrarily set to 0.0. FIG. 9C represents a scatter diagram of the logarithm of the resultant as a function of laboratory determined blood glucose.

In yet another embodiment, optical measurements when the blood flow is occluded can be another optical term that can be analyzed by the linear regression equation to predict blood glucose measurement. Applying a tourniquet (not shown) at the root of the finger F of the test subject in combination with the pulse oximetry finger clip provides additional important calibration information.

Figure 10:
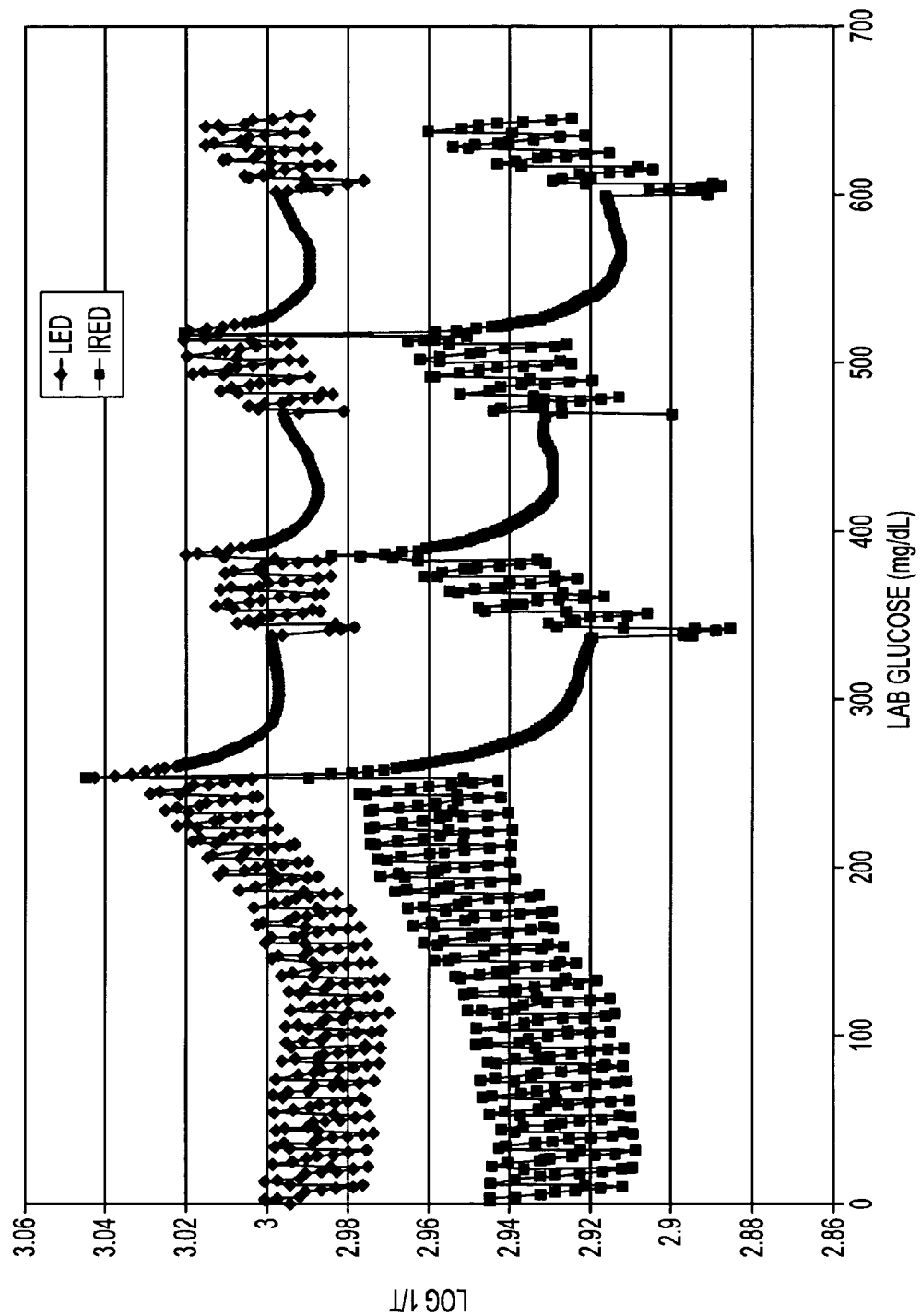
FIG. 10 shows pulse measurements of a test subject taken during the first fifteen seconds followed by three occlusion cycles when light energy is alternately emitted by both an IRED and a LED.
Figure 11A:
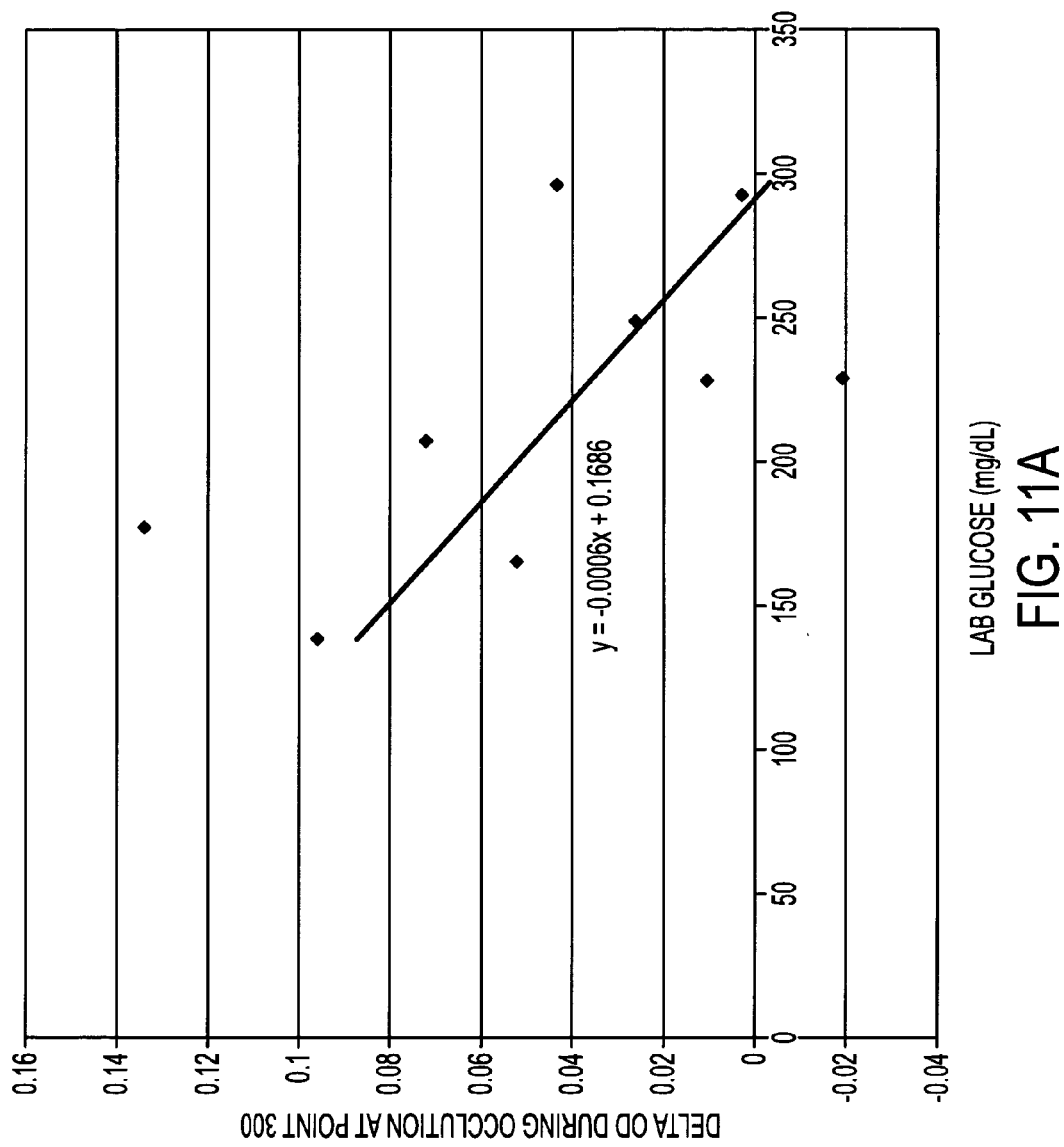
FIG. 11A is a scatter diagram of predicting glucose with a Delta OD term between the IRED and LED during the second of the three occlusion cycles.
Figure 11B:
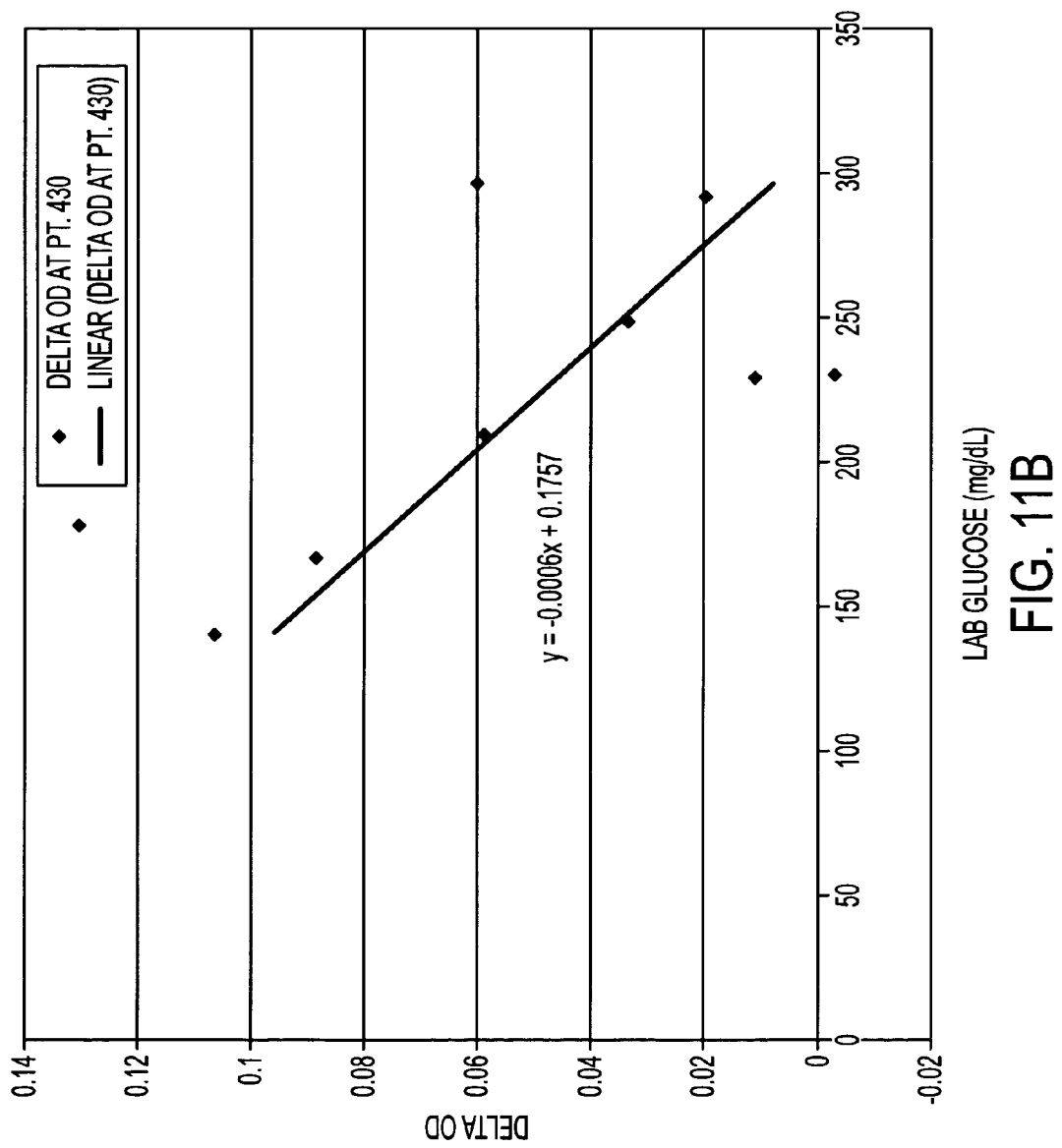
FIG. 11B is a scatter diagram of predicting glucose with a Delta OD term between the IRED and LED during the third of the three occlusion cycles.

FIG. 10 is a spectrum for the non-invasive measurement instrument that allows normal heart rate pulsing for the first 16 seconds followed by three occlusion cycles. FIGS. 11A and 11B are scatter diagrams of predicting glucose with a simple Delta OD term between the IRED 116 and LED 117 during the first three seconds of the occlusion cycle. FIG. 11A is measurement during the second occlusion cycle, and FIG. 11B is measurement during the third occlusion cycle. As illustrated in FIG. 11A, the offset of the line is 0.1686 and the slope is −0.0006. In FIG. 11B, the offset of the line is 0.1751 and the slope is the same as FIG. 11A. The correlation in FIG. 11A is −0.585, and the correlation in FIG. 11B is −0.567. A meaningful correlation can be obtained with a more complex mathematical term using the slope during the time of occlusion of the LED 117 divided by the slope at similar times of the IRED 116. Each of these analysis provide additional information for estimating or predicting blood glucose level.

It will be appreciated by those skilled in the art that the optical data of the IRED 116 and LED 117 can be analyzed in many other ways in addition to the above, such as i) normalizing the Delta Log 1/T value by dividing it by the average LED readings; ii) normalizing the Delta Log 1/T value by dividing it by the average IRED readings; iii) normalizing the Delta Log 1/T value by dividing it by the sum of the average LED and IRED readings; iv) dividing the IRED pulse strength by the LED pulse strength; v) normalizing the IRED pulse strength and dividing it by the normalized LED pulse strength; vi) dividing Delta OD by the average LED Log 1/T; vii) dividing Delta OD by the average IRED Log 1/T; viii) dividing Delta OD by the average IRED Log 1/T and average LED Log 1; etc. Each analysis shows that there is a meaningful correlation with laboratory glucose level.

In another embodiment, two or more of the previously described optical terms can be combined by multiple linear regression techniques.

The non-invasive measurement instrument of the present invention does not use any optical filters, lenses or diffuses, which usually absorb 99% of IRED energy, and only requires a single infrared emitting diode (IRED) and a single light emitting diode (LED), as opposed to multiple IREDs and multiple wavelengths required in prior art systems.

The non-invasive measurement instrument of the present invention is inexpensive and predicts the blood glucose concentration in blood. Further, the measurement instrument may also be used as a continuous monitoring device, which can be particularly important for individuals susceptible to hypoglycemia during their sleep.

Although the present invention has been described with reference to the particular embodiments disclosed, it is understood that these embodiments are merely illustrative of the application and principles of the invention. Numerous other configurations can be made and other arrangements can be devised without departing from the spirit and scope of the invention as defined in the appended claims.

What is claimed is:

1. A method for measuring a blood analyte concentration, comprising the steps of:
    obtaining energy absorption measurement data through a body part of an individual;
    calculating a plurality of indicator variables associated with a cyclic pulse signal from said energy absorption measurement data;
    determining which indicator variable from said plurality of indicator variables has the highest correlation to blood glucose level;
    allocating a first optical term based on said indicator variable with said highest correlation to blood glucose level to form a regression analysis equation; and
    calculating an estimated value of said blood analyte concentration using said regression analysis equation.

2. The method of claim 1, wherein said energy absorption measurement data is near-infrared energy absorption data and red light energy absorption data.

3. The method of claim 1, wherein said body part of said individual is a finger.

4. The method of claim 1, wherein said plurality of indicator variables are selected from the group consisting of pulse rate, LED pulse strength, IRED pulse strength, LED normalized pulse strength, IRED normalized pulse strength, pulse strength ratio, normalized pulse strength ratio, Delta OD, Delta OD divided by average LED Log 1/T, Delta OD divided by average IRED Log 1/T, Delta OD divided by average LED Log 1/T and average IRED Log 1/T, meal data, and occluded measurement data.

5. The method of claim 1, wherein said blood analyte concentration is a blood glucose concentration.

6. The method of claim 1, further comprising the step of calculating residual errors of said first optical term.

7. The method of claim 6, further comprising the steps of:
    determining for each remaining indicator variable from said plurality of indicator variables which has the highest correlation to said residual errors;
    allocating a second optical term based on said indicator variable with the highest correlation to said residual errors; and
    adding said second optical term to said regression analysis equation.

8. The method of claim 1, wherein said regression analysis equation is a linear residual regression equation.

9. The method of claim 1, wherein said regression analysis equation is a linear regression equation.

10. The method of claim 1, wherein said regression analysis equation is a multiple linear regression equation.

11. A non-invasive measurement instrument for measuring a blood analyte concentration, comprising:
    a first light source for introducing near-infrared energy into blood present in a body part of an individual;
    a second light source for introducing red light energy into said blood present in said body part;
    a detector for detecting said energy emerging from said body part, said detector producing an electrical signal indicative of said energy emerging from said body part; and
    a processor for calculating a plurality of indicator variables associated with a cyclic pulse signal from said electrical signal, determining which indicator variable from said plurality of indicator variables has the highest correlation to blood glucose level, and calculating an estimated value of said blood analyte concentration based on said indicator variable having said highest correlation to blood glucose level, wherein said blood analyte concentration is calculated using a regression analysis equation.

12. The measurement instrument of claim 11, wherein said plurality of indicator variables are selected from the group consisting of pulse rate, LED pulse strength, IRED pulse strength, LED normalized pulse strength, IRED normalized pulse strength, pulse strength ratio, normalized pulse strength ratio, Delta OD, Delta OD divided by average LED Log 1/T, Delta OD divided by average IRED Log 1/T, Delta OD divided by average LED Log 1/T and average IRED Log 1/T, meal data, and occluded measurement data.

13. The measurement instrument of claim 11, wherein said blood analyte concentration is a blood glucose concentration.

14. The measurement instrument of claim 11, further comprising a storage unit for storing said electrical signal, said plurality of indicator variables, and said regression analysis equation.

15. The measurement instrument of claim 11, wherein said processor calculates residual errors of said indicator variable having said highest correlation to blood glucose level.

16. The measurement instrument of claim 15, wherein a storage unit stores said residual errors.

17. The measurement instrument of claim 15, wherein said processor determines for each remaining indicator variable from said plurality of indicator variables which has the highest correlation to said residual errors, and calculates an estimated value of said blood analyte concentration based on said indicator variable having said highest correlation to said blood glucose level and said indicator variable having said highest correlation to said residual errors.

18. The measurement instrument of claim 11, further comprising an input device for entering meal data.

19. The measurement instrument of claim 11, further comprising a finger tourniquet for measuring occluded data.

20. The measurement instrument of claim 11, further comprising a display unit for displaying said estimated value of said blood analyte concentration.

21. The measurement instrument of claim 20, further comprising a warning device for notifying said individual of dangerous blood glucose levels.

22. The measurement instrument of claim 21, wherein the notification is at least one of a visual and audio indication.

23. The measurement instrument of claim 21, wherein said display unit and said warning device are in a second device.

24. The measurement instrument of claim 11, wherein said first light source, said second light source and said detector are in a first device, and said processor is in a second device connected to said first device through an electrical connection.

25. The measurement instrument of claim 11, wherein said body part of said individual is a finger.

26. The measurement instrument of claim 11, wherein said regression analysis equation is a linear residual regression equation.

27. The measurement instrument of claim 11, wherein said regression analysis equation is a linear regression equation.

28. The measurement instrument of claim 11, wherein said regression analysis equation is a multiple linear regression equation.

29. A method for measuring a blood analyte concentration, comprising the steps of:
   obtaining red and near-infrared energy absorption measurement data through a body part of an individual;
   calculating an indicator variable from said energy absorption measurement data;
   allocating a first optical term based on said indicator variable to form a regression analysis equation; and
   calculating an estimated value of said blood analyte concentration using said regression analysis equation,
   wherein said indicator variable is at least one of a pulse rate, LED pulse strength, IRED pulse strength, LED normalized pulse strength, IRED normalized pulse strength, pulse strength ratio, normalized pulse strength ratio, Delta OD, Delta OD divided by average LED Log 1/T, Delta OD divided by average IRED Log 1/T, Delta OD divided by average LED Log 1/T and average IRED Log 1/T, meal data, and occluded measurement data.

30. A non-invasive measurement instrument for measuring a blood analyte concentration, comprising:
   a first light source for introducing near-infrared (NIR) energy into blood present in a body part of an individual;
   a second light source for introducing red light energy into said blood present in said body part;
   a first detector for detecting said NIR energy emerging from said body part, said first detector producing a first electrical signal indicative of said NIR energy emerging from said body part;
   a first detector for detecting said NIR energy emerging from said body part, said first detector producing a first electrical signal indicative of said NIR energy emerging from said body part;
   a second detector for detecting said red light energy emerging from said body part, said second detector producing a second electrical signal indicative of said red light energy emerging from said body part; and
   a processor for calculating a plurality of indicator variables from said first electrical signal and said second electrical signal, determining which indicator variable from said plurality of indicator variables has the highest correlation to blood glucose level, and calculating an estimated value of said blood analyte concentration based on said indicator variable having said highest correlation to blood glucose level,
   wherein said blood analyte concentration is calculated using a regression analysis equation.

* * * * *